United States Patent [19]
Wiesent et al.

[11] Patent Number: 6,038,282
[45] Date of Patent: Mar. 14, 2000

[54] X-RAY IMAGING SYSTEM

[75] Inventors: Karl Wiesent, Erlangen, Germany; Ali R. Bani-Hashemi, Belle Mead; Nassir Navab, East Windsor, both of N.J.

[73] Assignees: Siemens Aktiengesellschaft, Munich, Germany; Siemens Corporate Research, Inc., Princeton, N.J.

[21] Appl. No.: 09/069,282

[22] Filed: Apr. 29, 1998

[30] Foreign Application Priority Data

Apr. 30, 1997 [DE] Germany ............................ 197 18 418

[51] Int. Cl.⁷ .............................. G01N 23/04; H61B 6/03
[52] U.S. Cl. .................................. 378/62; 378/4; 378/901
[58] Field of Search .................... 378/4, 62, 901

[56] References Cited

U.S. PATENT DOCUMENTS 5,706,324  1/1998  Wiesent et al. ............................ 378/4
5,963,612  10/1999 Navab ......................................... 378/4
5,963,613  10/1999 Navab ......................................... 378/4

OTHER PUBLICATIONS

"Dynamic Geometrical Calibration for 3–D Cerebral Angiography," Navab et al., SPIE, vol. 2708/361, pp. 361–370, Feb. 1996.

"Practical Cone–Beam Algorithm," Feldkamp et al, J. Opt. Soc. Am. A/vol. 1, No. 6, Jun. 1984, pp. 612–619.

*Primary Examiner*—David V. Bruce
*Attorney, Agent, or Firm*—Hill & Simpson

[57] ABSTRACT

In an X-ray imaging system with a C-arm which exhibits mechanical instability and changes the radiation geometry, the image reconstruction ensues with a calculation of the coordinates of the individual voxels being forgone. A voxel-driven back projection ensues without the calculation of positional coordinates and physical focus position and detector position.

5 Claims, 2 Drawing Sheets

X-RAY IMAGING SYSTEM

BACKGROUND OF THE INVENTION

1. Field of the Invention

The present invention is directed to an X-ray imaging system of the type wherein an X-ray radiator and a radiation receiver are mounted on a holding device and are rotated around a measuring field, in which an examination subject is disposed, for transirradiating the measuring field from different directions, and wherein an image of the examination subject is produced in a computer from the images obtained from the different directions.

2. Description of the Prior Art

There are known X-ray imaging systems in which an image receiver is provided, e.g. from a matrix of detector elements on the basis of amorphous, hydrogenated silicon, or an X-ray image intensifier is provided which is struck by a pyramid-shaped X-ray beam bundle, an X-ray image being created from the output signals of this intensifier with the aid of a computer. One such system is, for example, a C-arm apparatus with an X-ray source at the one end and a surface detector at the other end of a C-arm. Such X-ray imaging systems are mechanically unstable, given motion of the C-arm; i.e., the radiation geometry can change due to slight displacements of the focus or the detector. On the other hand, the open structure guarantees a good patient accessibility; i.e., the system is also suitable for use during an interventional procedure. In order to construct qualitatively good images with high spatial resolution, in known reconstruction algorithms the respective position of the focus and the detector relative to a fixed spatial coordinates system must be detected in a measurement conducted in the same fashion as the (subsequent) patient examination, and entered into the reconstruction algorithm. This occurs in a back projection, which can be realized either as a software solution on a general-purpose computer or with special hardware.

The focus in a computer tomography apparatus describes a perfect orbit about the isocenter without mechanical instabilities. The axis perpendicular to the plane of the circle through the isocenter is called the axis of rotation of the system. The detector is located at a constant distance. The detection surface is thus always perpendicular to the center beam which travels from the focus through the isocenter (optical axis).

For this type of reception geometry, an algorithm which consists essentially of a row-by-row preprocessing (convolution) and a back projection is described in L. A. Feldkamp, L. C. Davis, and J. W. Kreβ, "Practical Cone-Beam Algorithm"; J. Opt. Soc. Amer. A, Vol. 1, No. 6, pp 612–619, 1984.

If a C-arm device is used, two substantial deviations from this ideal geometry arise which force a modification of the Feldkamp Algorithm:

1. Partial revolution; i.e., the tubes and the detector do not revolve 360 degrees, but fewer, e.g. approximately 200° —at least 180°, plus the aperture angle of the radiation cone. This problem is solved by an appropriate weighting of the measurement values (sinogram weighting).

2. Mechanical instabilities lead not only to deviations from the orbit for the focus path, but also to tilting of the detector. The optical axis generally no longer runs through the isocenter, for example. This necessitates two measures:

a) Determination of the "true" reception geometry (actual geometry).

b) Consideration of the actual geometry in the back projection.

The determination of the reception geometry can be made with the aid of a marker ring, for example. If the fluctuations prove to be reproducible, then a tabulation of the geometry is possible by means of a calibration measurement.

The volume to be reconstructed is divided into discrete cubes—known as voxels (=volume element, in 2D: pixel= picture element). A voxel-driven back projection algorithm has the following form:

```
>loop over all projections:
    >determine position of projection center and detector
    >loop over all voxels
        >determine coordinates x,y,z of the voxel centerpoint
        >determine the line from projection center through (x,y,z)
        >determine the point of intersection of this line with the detector
        >determine value to be back-projected
    >back projection
    >end voxel loop
>end projection loop
```

The 2D surface detector is likewise made discrete, e.g. through 1024 rows and 1024 columns. The connection line of a voxel with the projection center generally does not intersect a measurement value position, but an intermediate position. A bilinear interpolation between the four neighboring positions is common.

A central projection can be mathematically described by a 3×4 projective matrix P. This matrix is delivered by the position detection system. German OS 19 512 819 teaches the determination of the actual geometry with the aid of a marker ring. By the relationship b=P * r, an image point b of the 2D detector is allocated to each point r of the 3D space. Homogenous coordinates are used, i.e. r=(x,y,z,1) and b=(u, v, w)=w * (u/w, v/w, 1). The normalized coordinates u/w and v/w can be interpreted directly as row numbers and column numbers of the detector. The projective matrix P can be interpreted as product of two matrices: P=A[R, T], wherein, R is a 3×3 rotation matrix, T is a 3×1 translation vector, and A is a 3×3 upper triangle matrix containing the intrinsic parameters (camera, imaging relations, etc.). In order to determine the spatial position of focus and detector, this dismantling of P must be carried out. A method therefor is described in SPIE, Vol. 2708, pages 361 to 370. This resolution into intrinsic and extrinsic parameters has in practice proven to be a numerically unstable process. This means that the resulting translation vector T and the rotation matrix R, for example, can be subject to substantially greater errors than the original result matrix P of the position detection system.

SUMMARY OF THE INVENTION

It is an object of the present invention to provide an X-ray image receiving system wherein the above-described resolution into the described parameters can be avoided.

The above object is achieved in accordance with the principles of the present invention in an X-ray system having an X-ray radiator and a planar radiation receiver, operating as a digital radiation detector, which are mounted on a shiftable holding device for transirradiating a measuring field from different directions, and having a computer for reconstructing an image of an examination subject in the measuring field from the signal supplied by the radiation receiver, the projection geometry for the transirradiation from different directions being described in homogenous coordinates by projection matrices, and wherein the computer executes a voxel-driven back projection, also in homogenous coordinates, without any calculation of positional coordinates.

A voxel-driven back projection algorithm is inventively provided which operates without the explicit calculation of focus coordinates and voxel coordinates.

DESCRIPTION OF THE PREFERRED EMBODIMENTS

Figure 1:
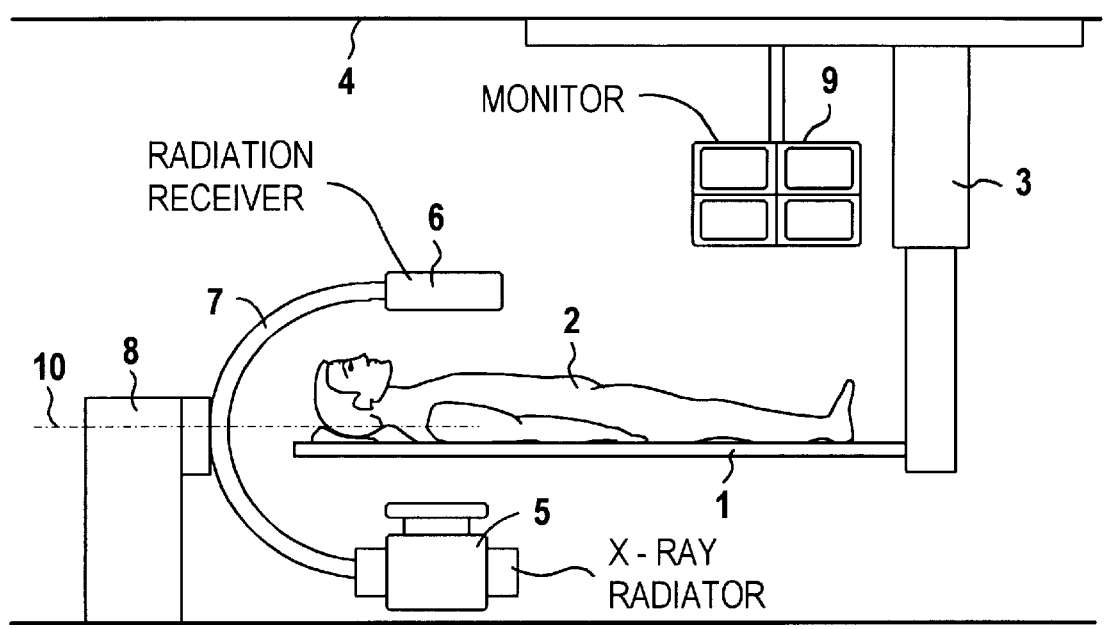
FIG. 1 shows the basic components of an X-ray image creation system with a C-arm, for explaining the invention.

FIG. 1 shows an orientation table 1 on which a patient 2 lies. The orientation table 1 is suspended from the ceiling 4 of the examination space by a stand 3. An X-ray 5 and a radiation receiver 6 are provided for the preparation of X-ray images. The X-ray 5 and the radiation receiver 6 are secured at a C-arm 7 which is displaceably mounted at a base 8. The image reproduction ensues on a monitor 9.

Volume data for the creation of three-dimensional images can be obtained when the X-ray 5 and the radiation receiver 6 are rotated around the system axis 10.

Figure 2:
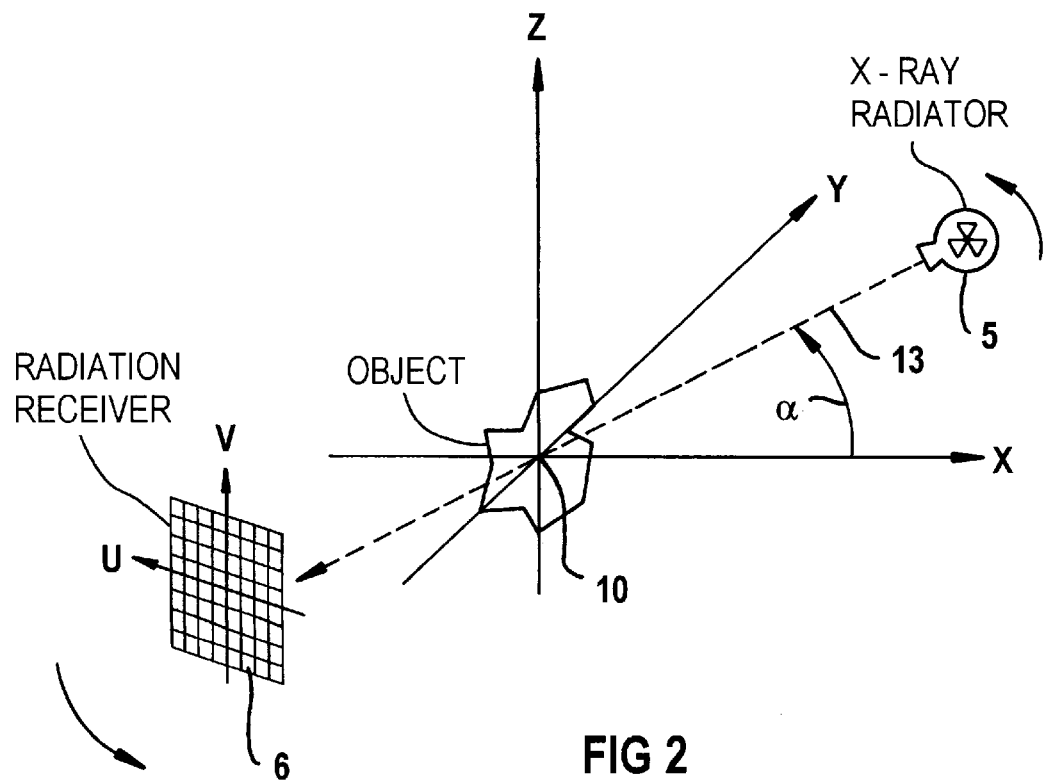
FIG. 2 shows the radiation geometry of the system according to FIG. 1, forming the basis of the invention.

FIG. 2 depicts the system axis—which proceeds perpendicularly to the projection plane—and the X-ray 5, as well as the radiation receiver 6. The radiation receiver 6 is a surface detector which is formed by a matrix of detector elements. FIG. 2 depicts another right-angled coordinate system (x, y, z), wherein the z-axis coincides with the system axis 10. The angle α is the angle between the x-axis and the center beam 13, and u, v are the coordinate system for the radiation receiver 6.

A voxel-driven back projection algorithm is provided in the invention which operates without the explicit calculation of focus coordinates and voxel coordinates. For each direction of projection, the following calculation steps are performed:

1. The 3×4 projection matrix P is supplied as an input, with the entries a11 a12 a13 b1
a21 a22 a23 b2
a31 a32 a33 b3

2. dx, dy, dz are the defined lengths of the voxel edges. They are multiplied at the first three columns of P, and a 3×3 auxiliary matrix Q is thus calculated:

ax1 ay1 az1
ax2 ay2 az2
x3 ay3 az3 with axi=ai1 *dx, ayi=ai2 *dy, azi=ai3 *dz.

3. P(i, j, k):=(xi, yj, zk) are the coordinates of the voxel with the indices (i, j, k), 1<=i<=nx, 1<=j<=ny, 1<=k<=nz. Specifically, P(0, 0, 0) (x0, y0, z0) are the coordinates of a hypothetical voxel outside the volume to be reconstructed, so that P (i, j, k)=(xi, yj, zk)=(x0+i *dx, y0+j*dy, z0+k*dz).

In homogeneous coordinates, the voxel (xi, yj, zk, 1) is imaged through the projection matrix P onto the image point I (i, j, k)=(ri, sj, tk). In this step, this imaging for the basis voxel is performed:

I(0,0,0)=(r0, s0, t0):=P*(x0, y0, z0, 1)

4. Voxel loop (pseudo-code, vector notation):

```
do i = 1, nx
    I (i, 0,0) = (r0, s0, t0) + i * (ax1, ax2, ax3)
    do j = 1, ny
        I (i,j,0)=I(i,0,0) + j * (ay1, ay2, ay3)
        do k=1, nz
            I (i,j,k) = (ri, sj, tk) = I(i,j,0) + k * (az1, az2, az3)
            u = ri/tk
            v = sj/tk
            backproject imagepoint (u, v)
        end do
    end do
end do
```

The floating point values u, v are generally non-whole-number row and column numbers of the 2D detector. If int (x) designates the largest whole number which is less than or equal to x, then int (u), int (u)+1, int (v), int (v)+1 are the rows and columns which have to be interpolated between these. In applications for cerebral angiography, an object which is 256*256*256 voxels in size is typically calculated from approximately 80 projections. The preliminary calculations in the steps 1–3 above are thus insignificant. What is significant is the compact code within the voxel loop. This is obtained through the continuous use of homogenous coordinates. Only at the absolute end is there a transfer to the normal detector coordinates system in the innermost loop, by normalizing. The explicit calculation of the spatial position of X-ray focal spot and detector is forgone, as is the calculation of the voxel coordinates.

The invention is not limited to the case of 3D. In other dimensions, the dimensionality of the applied matrices and vectors need only be adjusted accordingly. It is particularly suited to the case of 2D (linear detector, calculation from tomogram images.

The invention can also be used for stable devices (CT scanners with fixed gantry). In this case, the entire position detection system is forgone, and the entries of the projection matrix P are calculated from the device geometry and measurement geometry, which are then known.

FIG. 1 shows that the X-ray 5 and the radiation receiver 6 are mounted at the respective ends of the C-arm 7, which can be rotated in different directions by a motor for transirradiation of the measuring field and thus of the patient 2. This enables a lateral access to the patient 2 given a standing C-arm 7. Admittedly, a certain mechanical instability is associated therewith. The described voxel-driven back projection inventively ensues therein without calculation of positional coordinates. The respective projection geometry is described in homogeneous coordinates through 3×4 matrices (projection matrices). An efficient back projection likewise ensues in homogenous coordinates, i.e. without calculation of the coordinates of the individual voxels.

Figure 3:
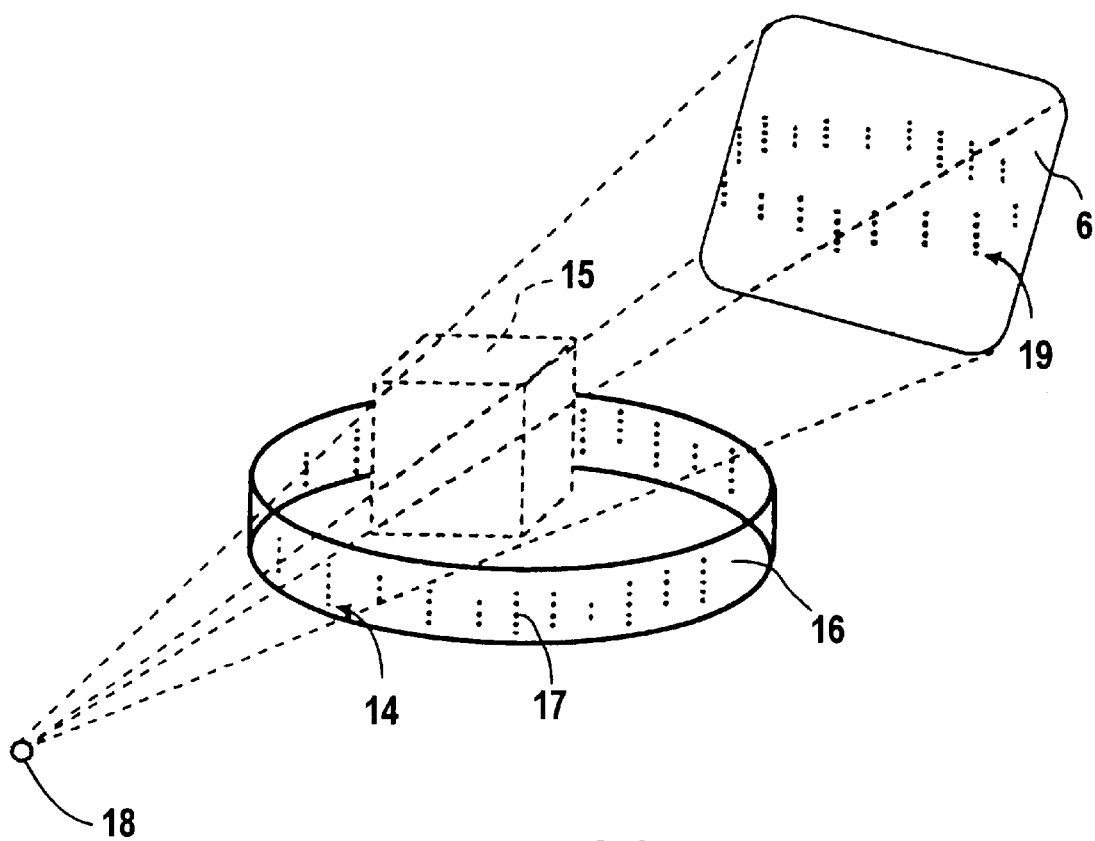
FIG. 3 schematically illustrates the acquisition of a projection matrix with a marker body, in accordance with the invention.

FIG. 3 shows the acquisition of the projection matrix with a marker body 14. This marker body 14 (not shown in FIG. 1) is arranged around the region of the patient to be examined, this region being schematically illustrated as a cube 15 in FIG. 3. The marker body 14 is formed, for example, by an annular supporting member 14 of a material transparent for X-rays, for example acrylic, and contains bodies, for example steel balls, that are highly absorbent for X-rays and that are arranged in a predetermined, known pattern. These bodies, one thereof being referenced 17, are arranged such that the projection matrix can be identified practically from arbitrary X-ray sub-images of the marker body 14. The X-rays in FIG. 3 are shown as emanating from a focus 18 (of the X-ray source 5). The projection matrix can be acquired because the image 19 of the bodies 17 on the radiation receiver 6 arises from the application of the projection matrix which is sought.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray imaging system comprising:

an X-ray radiator which emits an X-ray beam;

a radiation receiver comprising a digital detector of X-rays emitted by said X-ray radiator;

holding means, on which said X-ray radiator and said radiation receiver are mounted, for moving said X-ray radiator and said radiation receiver relative to a measuring field for transirradiating said measuring field in a plurality of different directions, and with a projection geometry associated therewith, said radiation receiver producing signals corresponding to radiation incident therein in each of said different directions; and a computer, supplied with said signals from said radiation detector, which reconstructs an image of a subject in said measuring field from said signals, said computer comprising means for describing said projection geometry in homogenous coordinates by a plurality of projection matrices, and for executing a voxel-driven back projection in homogenous coordinates without any calculation of positional coordinates.

2. An X-ray imaging system as claimed in claim 1 wherein said radiation receiver comprises a two-dimensional, planar digital detector.

3. An X-ray imaging system as claimed in claim 1 wherein said radiation receiver comprises a one-dimensional linear detector.

4. An X-ray imaging system as claimed in claim 1, wherein said computer comprises means for each projection direction, a) for calculating an auxiliary matrix Q ax1 ay1 az1
ax2 ay2 ax2
ax3 ay3 az3 with axi=ai 1*dx, ayi=ai2*dy, axi=ai3*dz by multiplication of the first three columns of a projection matrix (P)

a11 a12 a13 b1
a21 a22 a23 b2
a31 a32 a33 br with voxel edge lengths (dx, dy, dz);

b) means for defining the coordinates of a volume to be investigated, in said measuring field, in uniform coordinates, with an origin of the uniform coordinates having coordinates of a hypothetical voxel lying outside the volume to be investigated; and c) means for processing a voxel loop

```
do i=1, nx
    I(i,0,0)=(r0,s0,t0)+i*(ax1,ax2,ax3)
    do j=1,ny
        I(i,j,0)=I(i,0,0)+j*(ay1,ay2,ay3)
        do k=1,nz
            I(i,j,k)=(ri,sj,tk)=I(i,j,0)+k*(az1,az2,az3)
            u=ri/tk
            v=sj/tk
            backproject imagepoint (u,v)
        end do
    end do
end do,
wherein
``` i,j,k are voxel indices respectively corresponding to the three running indices in said loop respectively running from 1 to nx, 1 to ny and 1 to nz, wherein a value 0 corresponds to artificial base voxels outside a reconstruction volume, nx, ny and nz are a plurality of voxels of the reconstructed volume in the x, y, z directions, respectively, I(i,j,k)=(ri,sj,tk) are the uniform coordinates of a 2D point that is to be projected onto the voxel with the indices (i,j,k), u is a continuous horizontal coordinate within a 2D projection in pixel units, and v is continuous vertical coordinate within the 2D projection in pixel units.

5. An X-ray imaging system as claimed in claim 1 further comprising a marker body disposed at a geometrically known position in said measuring field, and wherein the computer comprises means for determining the projection matrix belonging to a projection direction directly from a detected image of said marker body in said geometrically known position.

* * * * *